United States Patent
Biry et al.

(10) Patent No.: US 8,574,205 B2
(45) Date of Patent: Nov. 5, 2013

(54) DEVICE FOR THE CUTANEOUS APPLICATION OF SUBSTANCES

(75) Inventors: Jean-François Biry, Paris (FR); Pascale Ehouarn, Gif sur Yvette (FR); Nathalie Donne, Allauch (FR); Bertrand Dupont, Aix en Provence (FR)

(73) Assignee: DBV Technologies, Boulogne Billancourt (FR)

( * ) Notice: Subject to any disclaimer, the term of this patent is extended or adjusted under 35 U.S.C. 154(b) by 562 days.

(21) Appl. No.: 12/530,727

(22) PCT Filed: Mar. 12, 2008

(86) PCT No.: PCT/FR2008/050419
§ 371 (c)(1),
(2), (4) Date: Mar. 22, 2010

(87) PCT Pub. No.: WO2008/132358
PCT Pub. Date: Nov. 6, 2008

(65) Prior Publication Data
US 2011/0046578 A1 Feb. 24, 2011

(30) Foreign Application Priority Data
Mar. 13, 2007 (FR) ...................................... 07 53787

(51) Int. Cl.
*A61M 35/00* (2006.01)
*A01K 29/00* (2006.01)

(52) U.S. Cl.
USPC ............................ 604/290; 604/308; 119/654

(58) Field of Classification Search
USPC ........... 119/654–655; 604/290, 304, 305–306
See application file for complete search history.

(56) References Cited

U.S. PATENT DOCUMENTS

| | | | | |
|---|---|---|---|---|
| 153,439 A * | 7/1874 | Juergenson | | 604/308 |
| 432,798 A * | 7/1890 | Hirst | | 604/308 |
| 588,091 A * | 8/1897 | Sanche | | 604/305 |
| 953,818 A * | 4/1910 | Chambers | | 119/819 |
| 1,081,148 A * | 12/1913 | Quayle | | 604/308 |
| 1,093,743 A * | 4/1914 | Tegarden | | 119/654 |
| 1,780,407 A * | 11/1930 | Smith | | 239/36 |
| 2,138,040 A * | 11/1938 | Perry | | 119/654 |
| 2,288,745 A * | 7/1942 | Sammis | | 62/331 |
| 2,641,074 A * | 6/1953 | Richmond | | 40/633 |
| 3,212,495 A * | 10/1965 | Osbourn et al. | | 600/556 |
| 3,491,753 A * | 1/1970 | Milton | | 602/46 |
| 3,598,122 A * | 8/1971 | Zaffaroni | | 424/435 |
| 3,886,935 A * | 6/1975 | Sprague | | 601/121 |
| 3,996,934 A * | 12/1976 | Zaffaroni | | 424/434 |
| 4,031,859 A * | 6/1977 | Stewart | | 119/654 |
| 4,140,116 A * | 2/1979 | Hampicke | | 602/62 |
| 4,297,995 A * | 11/1981 | Golub | | 604/304 |
| 4,430,961 A * | 2/1984 | Steckel | | 119/654 |
| 4,435,180 A | 3/1984 | Leeper | | |

(Continued)

FOREIGN PATENT DOCUMENTS

FR 2527450 12/1983
WO 2004/052425 6/2004

*Primary Examiner* — Melanie Hand
*Assistant Examiner* — Paula Craig
(74) *Attorney, Agent, or Firm* — Nixon & Vanderhye P.C.

(57) ABSTRACT

The present disclosure provides a device (1) for the cutaneous application of a substance (2) that contains: a patch (3) containing the substance (2); and a single-use wrist strap (4) containing an irreversible attachment system for maintaining the substance (2) of the patch (3) against the skin of a subject.

6 Claims, 1 Drawing Sheet

(56) References Cited

U.S. PATENT DOCUMENTS

| | | | |
|---|---|---|---|
| 4,450,844 A * | 5/1984 | Quisno | 600/556 |
| 4,486,194 A * | 12/1984 | Ferrara | 424/449 |
| 4,592,753 A * | 6/1986 | Panoz | 424/449 |
| 4,595,011 A * | 6/1986 | Phillips | 600/362 |
| 4,619,654 A * | 10/1986 | Abplanalp | 604/890.1 |
| 4,620,849 A * | 11/1986 | Corner | 604/290 |
| 4,666,441 A * | 5/1987 | Andriola et al. | 604/304 |
| 4,781,705 A | 11/1988 | Shepherd et al. | |
| 4,833,807 A * | 5/1989 | McLean | 40/633 |
| 5,135,480 A * | 8/1992 | Bannon et al. | 604/20 |
| 5,167,617 A * | 12/1992 | Sibalis | 604/20 |
| 5,194,265 A * | 3/1993 | Boettcher et al. | 424/411 |
| 5,259,835 A * | 11/1993 | Clark et al. | 602/48 |
| 5,396,901 A * | 3/1995 | Phillips | 600/584 |
| 5,448,846 A * | 9/1995 | Peterson et al. | 40/633 |
| 5,507,721 A * | 4/1996 | Shippert | 602/46 |
| 5,591,123 A * | 1/1997 | Sibalis et al. | 604/20 |
| 5,785,354 A * | 7/1998 | Haas | 283/74 |
| 5,899,875 A * | 5/1999 | Millot et al. | 604/20 |
| 5,914,197 A * | 6/1999 | Goudjil | 428/537.5 |
| 6,056,729 A * | 5/2000 | Yu et al. | 604/289 |
| 6,167,302 A * | 12/2000 | Millot | 604/20 |
| 6,349,493 B1 * | 2/2002 | Newman et al. | 40/633 |
| 6,693,543 B1 * | 2/2004 | Stephenson et al. | 340/572.9 |
| 7,658,027 B2 * | 2/2010 | Jain et al. | 40/633 |
| 7,905,111 B2 * | 3/2011 | Saltz | 63/3 |
| 2002/0173738 A1 * | 11/2002 | Rogalski | 602/21 |
| 2003/0114475 A1 * | 6/2003 | Fox et al. | 514/282 |
| 2004/0092896 A1 * | 5/2004 | Thompson | 604/304 |
| 2004/0189470 A1 * | 9/2004 | Girvin et al. | 340/568.2 |
| 2007/0156076 A1 * | 7/2007 | Jackson et al. | 602/54 |
| 2007/0248635 A1 * | 10/2007 | Jensen | 424/402 |
| 2009/0118685 A1 * | 5/2009 | Choi et al. | 604/308 |
| 2011/0004169 A1 * | 1/2011 | Smith et al. | 604/290 |

* cited by examiner

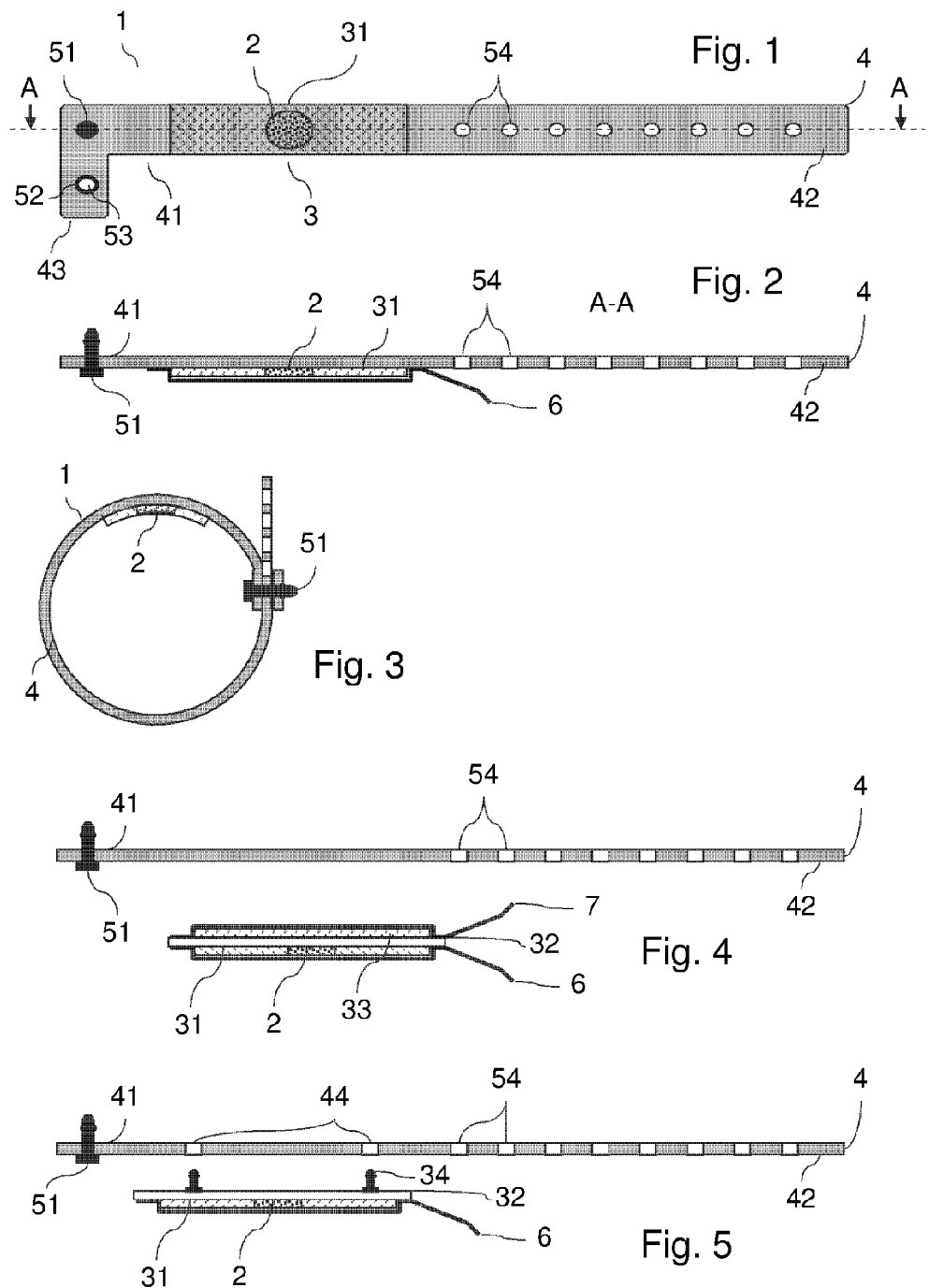

DEVICE FOR THE CUTANEOUS APPLICATION OF SUBSTANCES

The present application is a 371 U.S. National Phase of PCT/FR2008/050419, filed Mar. 12, 2008, which designated the U.S. and claims benefit of FR 0753787, filed Mar. 13, 2007.

The present invention generally relates to devices for epi- or trans-cutaneous application of biologically active substances. The invention more particularly relates to transdermal devices or patches intended to facilitate cutaneous absorption of such substances, notably for vaccination, desensitization or drug administration purposes.

The human epidermis forms a barrier against the entry of exterior agents into the body. The skin is not impervious, but in fact pervious to a very large number of substances with variable permeability level.

Percutaneous absorption corresponds to the transfer of a substance through the skin from the exterior medium as far as the blood. This absorption is defined as the sum of two phenomena: a penetration of molecules into the interior of the entire skin, followed by resorption by the blood or lymph circulatory flow from the papillar dermis and then from the deep dermis. The penetration step physically is a passive diffusion through each structure of the tegument: the stratum corneum, Malpighi's epidermis, the dermis and cutaneous annexes. Once it is absorbed, the substance is distributed into the body, and then, after having either been metabolized or not, it is eliminated. The steps succeeding to percutaneous absorption are similar to those encountered for any other contamination route.

The stratum corneum is the most effective barrier against the penetration of a substance; anatomically, the substance may penetrate through two routes: one through the intercellular spaces of the stratum corneum and through the corneous cells themselves, the other one via the cutaneous annexes. In the case of a vaccine, once this stratum corneum is crossed, the substance is able to encounter immunologically competent cells, and in particular cells exhibiting antigens such as Langerhans cells, the role of which is primordial in the immunological reaction of the organism. By facilitating the initial passage of the antigen through the stratum corneum, epicutaneous vaccination is made more effective. In the case of a patch intended for administering a molecule for a systemic treatment, by temporarily reducing the effectiveness of the stratum corneum as a barrier, it is possible to open the route to transcutaneous administration of active ingredients with high molecular weights, and generally improve the administration rate of active ingredients.

Percutaneous absorption of a substance by means of a patch has significant advantages relatively to a needle injection: absence of any risk of contamination by damaging the skin, absence of pain, ease in transport, prolonged preservation of the active substance or further administration of the substance by the patient himself/herself.

However, such an administration mode also has drawbacks. Indeed, unlike a sub-cutaneous injection, a minimum period of application is required in order to end up with the effect of the substance of the patch. Thus, vaccination or immunization may be incomplete if the patch has not been applied for sufficient time on the skin. As the required period of application is much longer than the duration of an injection, a practitioner cannot remain close to the patient for this duration. The practitioner is then not quite sure that the patient has kept the patch in contact with the skin for a sufficient time.

Patent FR 2,527,450 relates to a device for releasing a substance in the skin, consisting of, for example, an elastomeric bracelet loaded with an active substance. However, the proposed device is reusable and is therefore not able to prevent early removal of the patch, or to ensure that a sufficient contact time was observed by the patient.

The invention aims at solving one or more of these drawbacks. The object of the invention is thus a device for cutaneous application of a substance, comprising:
  a patch comprising said substance; and
  a single-use bracelet comprising an irreversible attachment system with which the substance of the patch may be maintained against the skin of a subject.

The invention thus proposes a device for cutaneously applying a substance making it possible, by a single-use irreversible attachment system, to prevent early removal of the device by the patient and/or to ensure that a sufficient time of contact with the skin has been observed.

According to one alternative, the bracelet comprises two attachment portions and the irreversible attachment system of the bracelet comprises means for attaching together both attachment portions irreversibly, the bracelet forming a loop when both attachment portions are joined together.

According to another alternative, the attachment portions comprise mutually adhesive surfaces.

According to still another alternative:
  one of the two attachment portions comprises a locking member having a bore, and comprises a stud able to be inserted through the bore irreversibly;
  the other of the two attachment portions comprises at least one bore capable of letting through the stud.

According to still another alternative, the locking member has a ring delimiting the bore and elastically deformable so as to allow irreversible insertion of the stud.

According to an alternative, the device comprises means for securing the patch to the bracelet.

According to still another alternative, the means for securing the patch to the bracelet are irreversible.

According to another alternative, the irreversible securing means comprise a surface of the patch or bracelet coated with an adhesive and covered with a peelable protective element.

According to a further alternative, the irreversible securing means of the patch to the bracelet comprise a member of the patch and a member of the bracelet which may be snapped on mutually.

According to still another alternative, the device comprises a packaging containing the bracelet and the patch.

According to an alternative, the bracelet has a surface in contact with the substance.

According to a further alternative, the bracelet has an adhesive surface in proximity to the substance.

According to another alternative, the adhesive surface surrounds the substance.

According to still another alternative, the patch comprises a support provided with a face having a surface in contact with the substance and an adhesive surface intended to enter into contact with the skin.

According to an alternative, the patch comprises a peelable protective element if necessary secured to the support or the bracelet and covering the substance.

According to a further alternative, the bracelet covers the substance.

Another object of the invention relates to the use of a device as defined hereinbefore for applying a substance on the skin and/or for delivering a substance via an epi- or trans-cutaneous route to a subject, notably a mammal, in particular a human being (a child or an adult for example). The device may notably be used for vaccinating subjects, for desensitizing subjects, for testing the sensitivity of subjects to substances or for delivering any active substance, such as notably biologically active and/or antigenic (poly)peptides, for example.

The device may also be used for vaccinating subjects against any pathogen. Thus, a particular object of the invention lies in a method for vaccinating a subject against a pathogen, comprising (i) the application of the device according to the invention on the skin of a subject, the substance comprising a specific antigen of said pathogen, (ii) the irreversible attachment of the bracelet around a limb of the subject and the maintaining of the bracelet, preferably at the same location, for a time period allowing transfer of the antigen into the body. The pathogen may be of variable nature (virus, bacteria, parasite, etc.) and the antigen is typically of a polypeptide or lipid nature.

The device may also be used for desensitization of subjects to allergens. Thus, a particular object of the invention lies in a method for desensitizing a subject to an allergen, comprising (i) the application of a device according to the invention on the skin of a subject, the substance comprising a specific antigen of said allergen, (ii) the irreversible attachment of the bracelet around a limb of the subject and the maintaining of the bracelet, preferably at the same location, for a time period allowing transfer of the antigen into the skin.

The device may also be used for delivering any active substance. Thus, a particular object of the invention lies in a method for delivering an active substance to a subject, comprising (i) the application of a device according to the invention on the skin of a subject, the substance comprising a specific antigen of said allergen, (ii) the irreversible attachment of the bracelet around a limb of the subject and the maintaining of the bracelet, preferably at a the same location, for a time period allowing transfer of the substance into the skin. The substance is typically of a polypeptide nature, such as a hormone, a cytokine, a growth factor, a trophic factor, etc.

The substance contained in the patch may be formulated in any suitable carrier or excipient, and may be in solid form (powder), liquid form (for example a gel, slurry, solution), etc.

Another object of the invention relates to a method for making a device as defined above, comprising a step of functional assembling between a patch and a single-use bracelet with irreversible attachment.

Other features and advantages of the invention will become clearly apparent from the description which is made thereof hereafter, as an indication and by no means as a limitation, with reference to the appended drawings, wherein:

FIG. 1 is a bottom view of a first embodiment of the cutaneous application device according to the invention, ready to be set into place;

FIG. 2 is a transverse sectional view of the device of FIG. 1;

FIG. 3 is a transverse sectional view of the bracelet after its setting into place;

FIG. 4 is a transverse sectional view of a device formed by a kit, according to a second embodiment;

FIG. 5 is a transverse sectional view of a device formed with a kit according to a second embodiment.

Subsequently, the terms of irreversible or untamperable attachment will define an attachment which has to be at least partly destroyed in order to be undone.

The invention proposes a device for cutaneously applying a substance, making it possible to determine or ensure with certainty that a substance has been applied for a sufficiently long time. The device comprises a patch including said substance intended to penetrate or enter into contact with the epidermis, and a single-use bracelet provided with an irreversible attachment system with which it is possible to avoid early removal of the device and/or ensure that a sufficient contact time of the substance against the skin of a subject has been observed.

The patch may be of any nature, and it may thus be any device or any support or surface applied on the skin of a subject in order to apply a substance thereon. This may be a patch, either occlusive or not, a transdermal device, a bandage, etc. The patch may consist of different materials (polymer(s), plastic, metal, patch, etc.), and the substance may be bound to the patch in different ways (impregnation, covalent bond, reservoir, electrostatic forces, etc.).

FIGS. 1-3 more specifically illustrate a first embodiment of a device 1 for cutaneously applying a substance 2. The device 1 includes a patch 3. The patch 3 comprises the substance 2 and an adhesive 31 intended to be applied on the skin. The adhesive 31 is positioned in proximity to the substance 2 in order to improve its maintaining in contact against the skin of the subject. Advantageously, the adhesive 31 surrounds the substance 2 in order to guarantee its optimum contact with the skin, but other configurations are of course possible (in strips, spots, etc.). The device 1 further comprises a single-use bracelet 4. The bracelet 4 is provided with an irreversible attachment system with which it is possible to prevent early removal of the device, and thus maintain the substance 2 against the skin of a subject for a sufficient period of time.

The bracelet 4 is substantially formed as a strip. The bracelet 4 comprises in a known way per se, two attachment portions 41 and 42, positioned on both ends of the strip. In a known way per se, the bracelet 4 is flexible so that the attachment portions 41 and 42 may be joined together. When the attachment portions 41 and 42 are joined together, the bracelet 4 forms a loop, as illustrated in FIG. 3. The irreversible attachment means comprise means for attaching together the portions 41 and 42 irreversibly. These attachment means comprise a locking member positioned at the attachment portion 41. The locking member includes a stud 51 and a bore 53. The stud 51 and the bore 53 are conformed so that the stud 51 may be irreversibly inserted through the bore 53. The stud 51 thus comprises a widened end, followed by a thinner middle portion. The locking member has a ring 52 delimiting the bore 53 and being elastically deformable by the stud, so as to allow irreversible insertion of the stud 51 through the bore 53. Once the widened end of the stud 51 has crossed the bore 53, the ring is accommodated in the middle portion of the stud 51.

The ring 52 is positioned on a side protrusion of the portion 41. This side protrusion 43 is able to be folded back in order to insert the stud 51 into the bore 53 of the ring 52. The attachment portion 42 comprises several bores 54 distributed in the direction of the length of the bracelet 4. The different longitudinal positions of the bores allow the size of the loop to be adapted to the dimension of the limb of the subject. As illustrated in FIG. 3, the attachment of both portions 41 and 42 is irreversible when the stud 51 crosses both a bore 54 and the bore 53, the side protrusion 43 being folded back on the remainder of the portion 42.

Other irreversible attachment means of the attachment portions known to one skilled in the art in the field of untamperable bracelets may of course be used.

As illustrated in FIG. 2, the device 1 further comprises a peelable protective element 6. The peelable protective element 6 entirely covers the adhesive 31 and the substance 2 in order to avoid their deterioration before their application on the skin. The peelable element 6 is provided with a grip tab facilitating its peeling. In FIG. 1, the device is illustrated in the absence of the peelable element 6.

In this embodiment, the provided device initially comprises a patch 3 integral with the bracelet 4. The bracelet 4 in practice forms a support in contact with the adhesive 31 and the substance 2. Irreversibility of the attachment therefore guarantees application on the skin of the substance 2 of the patch until failure of the bracelet 4 or of the attachment system.

As a replacement or in addition to the irreversible mechanical attachment by means of the elements 51-54, it is also possible to contemplate both portions 41 and 42 having mutually adhesive surfaces. The person skilled in the art may determine an adequate adhesive so that an attempt to open the loop leads to visible deterioration of the bracelet or of the adhesive.

In the embodiments of FIGS. 4 and 5, the patch 3 and the bracelet 4 are provided as a kit. The patch 3 and the bracelet 4 of these embodiments have mutual securing means. These mutual securing means are advantageously irreversible, so that irreversibility of the attachment guarantees application on the skin of the substance 2 of the patch until failure of the bracelet 4 or of the attachment system. With these embodiments, it is for example possible to select a patch 3 having a desired dosage of the substance 2 and then to secure this patch 3 to a single-use bracelet 4 irreversibly. Advantageously, provision may be made for the bracelet 4 and the patch 3 to be positioned in a same non-illustrated package.

The device 1 according to the embodiment illustrated in FIG. 4 comprises a bracelet 4 similar to the one of the first embodiment. The device 1 further comprises a patch intended to be irreversibly secured to the bracelet 4. The patch 3 comprises a support 32 such as a synthetic film. A substance 2 and an adhesive 31 are secured to a first face of the support 32. An adhesive 33 is secured to a second face of the support 32. The adhesive 33 is intended to secure the patch 3 irreversibly to the bracelet 4. The bracelet 4 has a surface intended to ensure adhesion with the adhesive 33. After securing the bracelet 4 and the patch 3, this surface advantageously covers the substance 2 entirely. Thus, contact of the substance 2 with the skin is guaranteed during the wearing of the bracelet 4.

A peelable protective element 6 entirely covers the adhesive 31 and the substance 2. A peelable protective element 7 entirely covers the adhesive 33, in order to avoid its deterioration before its application against the bracelet 4. Like the peelable element 6, the peelable element 7 has a grip member for facilitating its peeling.

The device 1 according to the embodiment illustrated in FIG. 5 comprises a bracelet 4 similar to the one of the first embodiment. Two bores 44 are further provided in a middle area of the bracelet 4. The device 1 further comprises a patch 3 intended to be irreversibly secured to the bracelet 4. The patch 3 comprises a support 32, such as a synthetic film. A substance 2 and an adhesive 31 are secured to a first face of the support 32. Both studs 34 protrude from a second face of the support 32. The studs 34 and the bores 44 are configured in order to guarantee irreversible securing of the bracelet 4 and of the patch 3. The bores 44 for this may be delimited by rings similar to the ring 52.

In the embodiments of FIGS. 4 and 5, provision may be made for the support 32 to have electrostatic properties on the face in contact with the substance 2. An example of such a support is for example described in patent application WO 02/071950 or WO 2006/128981. It may then be provided that a substance 2 as particles should be maintained in contact with the support 32 by electrostatic forces. However, it is understood that the present application may be applied to any type of patch.

The invention claimed is:

1. A device (1) for cutaneously applying a substance (2) to a human subject, comprising: a patch (3) comprising said substance (2); and a single-use bracelet (4) to maintain the patch (3) in contact with the skin of the subject, the patch being linked to the bracelet and the bracelet comprising two attachment portions forming a loop when both attachment portions are joined together, wherein the bracelet comprises means for irreversibly attaching together said both attachment portions so that the bracelet cannot be removed without at least partly destroying the device, and wherein: one of the two attachment portions comprises a locking member (51, 52, 53) having a bore (53), and comprises a stud (51) capable of being irreversibly inserted through the bore; the other of the two attachment portions comprises at least one bore (54) capable of being crossed by the stud.

2. The device (1) according to claim 1, wherein the locking member has a ring (52) delimiting the bore (53) and elastically deformable so as to allow irreversible insertion of the stud (51).

3. The device (1) according to claim 1, wherein the patch (3) is linked to the bracelet (4) by a member (34) of the patch and a member (44) of the bracelet which are snapped on mutually.

4. The device (1) according to claim 1, comprising a packaging containing the bracelet (4) and the patch (3).

5. The device (1) according to claim 1, wherein the patch comprises a support (32) provided with a face having a surface in contact with the substance (2) and an adhesive surface (31) intended to enter into contact with the skin.

6. The device (1) according to claim 1, wherein the patch (3) comprises a peelable protective element (6) covering the substance (2).

* * * * *